(12) United States Patent
Bajwa et al.

(10) Patent No.: US 11,793,527 B2
(45) Date of Patent: Oct. 24, 2023

(54) INSTRUMENT FOR REMOVAL OF DORSAL NASAL HUMP

(71) Applicants: Afzaal Bashir Bajwa, Pasrur (PK); Sunaina Afzaal, Pasrur (PK); Sadia Rehman Shaikh, Pelham, AL (US)

(72) Inventors: Afzaal Bashir Bajwa, Pasrur (PK); Sunaina Afzaal, Pasrur (PK); Sadia Rehman Shaikh, Pelham, AL (US)

( * ) Notice: Subject to any disclaimer, the term of this patent is extended or adjusted under 35 U.S.C. 154(b) by 303 days.

(21) Appl. No.: 17/172,881

(22) Filed: Feb. 10, 2021

(65) Prior Publication Data
US 2021/0251641 A1    Aug. 19, 2021

(30) Foreign Application Priority Data
Feb. 13, 2020   (PK) ........................... 96/2020

(51) Int. Cl.
*A61B 17/16* (2006.01)
*A61B 17/24* (2006.01)

(52) U.S. Cl.
CPC .......... *A61B 17/1688* (2013.01); *A61B 17/24* (2013.01)

(58) Field of Classification Search
CPC .. A61B 17/1659; A61B 17/1688; A61B 17/24
See application file for complete search history.

(56) References Cited

U.S. PATENT DOCUMENTS

| | | | | |
|---|---|---|---|---|
| 505,818 | A * | 10/1893 | Dallas | A61B 17/1659 606/85 |
| 4,625,725 | A * | 12/1986 | Davison | A61B 17/1659 407/29.1 |
| 2006/0276817 | A1 * | 12/2006 | Vassallo | A61B 17/24 606/199 |
| 2011/0270256 | A1 * | 11/2011 | Nelson | A61B 17/1659 606/85 |

* cited by examiner

*Primary Examiner* — Nicholas W Woodall

(57) ABSTRACT

A surgical device for removal of dorsal nasal hump, comprising: a handle (1) 30 mm broad, 100 mm long and 10 mm thick; connected to a rounded neck (2), 40 mm long and 5 mm thick; a working end (3), 8 mm broad, positioned at the distal part of a handle (1) where a working end (3) is semicircular from top and flat on the under surface. Under surface of a working end (3) contains two parts: a wrasping part (3A) 30 mm thick, tapered and blunt at tip and a cutting part (3B), 30 mm thick where the cutting part is positioned between a neck (2) and a wrasping part (3A). The cutting part (3B) comprises a collecting chamber (3B1), 10 mm long, 6 mm wide and 3 mm deep and a sharp blade (3B2), 6 mm wide positioned at proximal edge of collecting chamber. A metallic lid (3B3), 20 mm long and 7 mm wide disposed longitudinally where a knob (2A) positioned on the metallic lid (3B3), slides the metallic lid back and forth to cover and uncover the blade simultaneously.

7 Claims, 2 Drawing Sheets

INSTRUMENT FOR REMOVAL OF DORSAL NASAL HUMP

FIELD OF INVENTION

Present invention relates to the field of medical instruments in particular to a field of Nose surgery, specifically, a device for removing hump on dorsum of nose.

BACKGROUND OF INVENTION

Dorsal Nasal Hump is cartilaginous or bony or both cartilaginous and bony prominence present at the dorsum of nose. (Palhazi, Daniel et al. 2015). The osseocartilaginous vault of the nose: anatomy and surgical observations. Most of the nasal hump have combination of osseous and cartilaginous components. (Rohrich, Muzaffar et al. 2004). Component dorsal hump reduction: the importance of maintaining dorsal aesthetic lines in rhinoplasty. Shaving and wrasping is usually done to address this deformity during rhinoplasty. (Arslan and Aksoy 2007). Upper Lateral Cartilage Sparing Component Dorsal Hump Reduction in Primary Rhinoplasty. Traditionally bony (osseous) component of hump is removed by wrasp or chisel while cartilaginous component is removed by knife or scissors which requires open rhinoplasty. Lot of dissection is needed for this procedure. (Ponsky, Eshraghi et al. 2010).

Dorsal nasal hump removal with this novel instrument not only avoids lot of cutting and opening of nose but also makes tunneling easy and wrasping of bony component and cutting of cartilaginous component simultaneously. This single instrument adequately removes both components with less tissue trauma and helps in quick recovery postoperatively.

DESCRIPTION OF INVENTION

Unlike previous methods known and described in prior art, the hump removal by this novel instrument requires a small cut on inner side of nose and tunnel formation with closed rhinoplasty technique. Both cartilaginous and bony components of dorsal nasal are removed. Wrasping part of device removes bony component and blade of cutting part when uncovered by moving the lid cuts the cartilaginous component of nasal hump.

Unless defined otherwise all technical and scientific terms used herein have the same meanings as commonly understood to one of ordinary skill in the art to which this invention belongs.

The details of one or more embodiments of the invention are set forth in the accompanying drawings and the description below. Other features, objects and advantages of the invention will be apparent from the description, drawings and from the claims.

Objects of the present invention include providing a surgical device with its components and a method of using the device. Claimed device of present invention is an innovative approach in removing both cartilaginous and bony components of dorsal nasal hump with minimal tissue cutting and quicker recovery.

A surgical device for removal of dorsal nasal hump, comprising: a handle (1) 30 mm broad, 100 mm long and 10 mm thick; connected to a rounded neck (2), 40 mm long and 5 mm thick; a working end (3), 8 mm broad, positioned at the distal part of a handle (1) where a working end (3) is semicircular from top and flat on the under surface. Under surface of a working end (3) contains two parts: a wrasping part (3A) 30 mm thick, tapered and blunt at tip and a cutting part (3B), 30 mm thick where the cutting part is positioned between a neck (2) and a wrasping part (3A). The cutting part (3B) comprises a collecting chamber (3B1), 10 mm long, 6 mm wide and 3 mm deep and a sharp blade (3B2), 6 mm wide positioned at proximal edge of collecting chamber. A metallic lid (3B3), 20 mm long and 7 mm wide disposed longitudinally where a knob (2A) positioned on the metallic lid (3B3), slides the metallic lid back and forth to cover and uncover the blade simultaneously.

The tapering end helps in making a tunnel in the soft tissues of nose. Wrasping part (3A) removes bony component of hump. Metallic lid (3B3) covers sharp blade (3B2) and chamber (3B1). When knob (2A) is moved backward, sharp blade (3B2) and chamber (3B1) is uncovered. Blade (3B2) cuts the cartilaginous component of hump and chamber (3B1) collects the cut pieces of cartilage.

If hump has only bony component, keep the metallic lid (3B3) closed and remove the hump with wrasping part (3A) only. If the hump has only cartilaginous component, move the knob (2B) uncover the sharp blade (3B2) and chamber (3B1) and cut the cartilaginous component of the hump and there is no need of wrasping. Further, this novel instrument can remove bony and cartilaginous hump simultaneously.

A surgical device as claimed in claim 1, for the use in removal of dorsal nasal hump, comprising following steps:
holding the novel instrument at handle (1) and introduce into the small cut made inside the nose;
keeping the metallic lid (3B3) closed;
pushing the working end (3) through its tapering part for making a tunnel inside a nasal dorsum;
uncovering the sharp blade (3B2) and chamber (3B1) by moving knob (2A) backward while the instrument is inside a nasal dorsum;
cutting the cartilaginous part of hump by to and fro movements of working end;
closing the metallic lid (3B3) by moving the knob (2B) forward, covering sharp blade (3B2) and chamber (3B1) both, and afterwards,
wrasping the bony component of hump with wrasping part (3A) by to and fro movements inside the tunnel.

DESCRIPTION OF DRAWINGS

Description of drawings is as follows:

FIG. 1 mentions all parts of device like Handle (1), Neck (2) and Working End (3).

Figure 1:
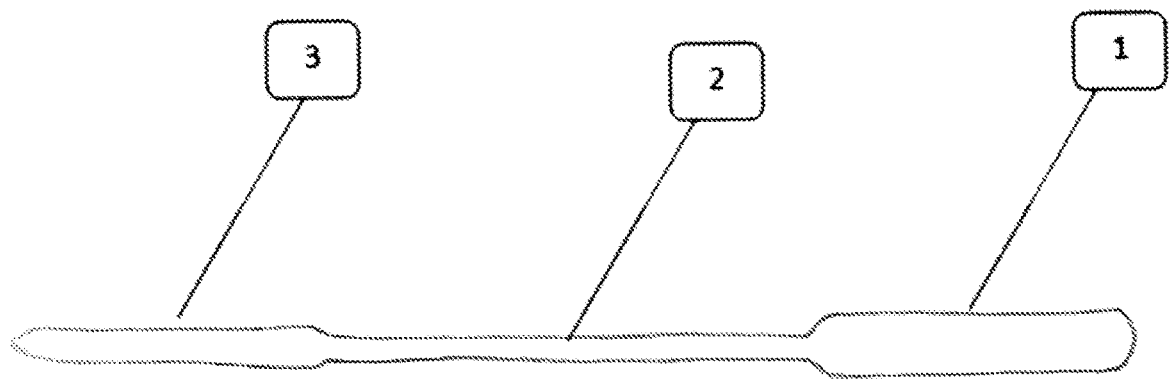
FIG. 1 shows the Dorsal (upper) view of the claimed device.
Figure 2:
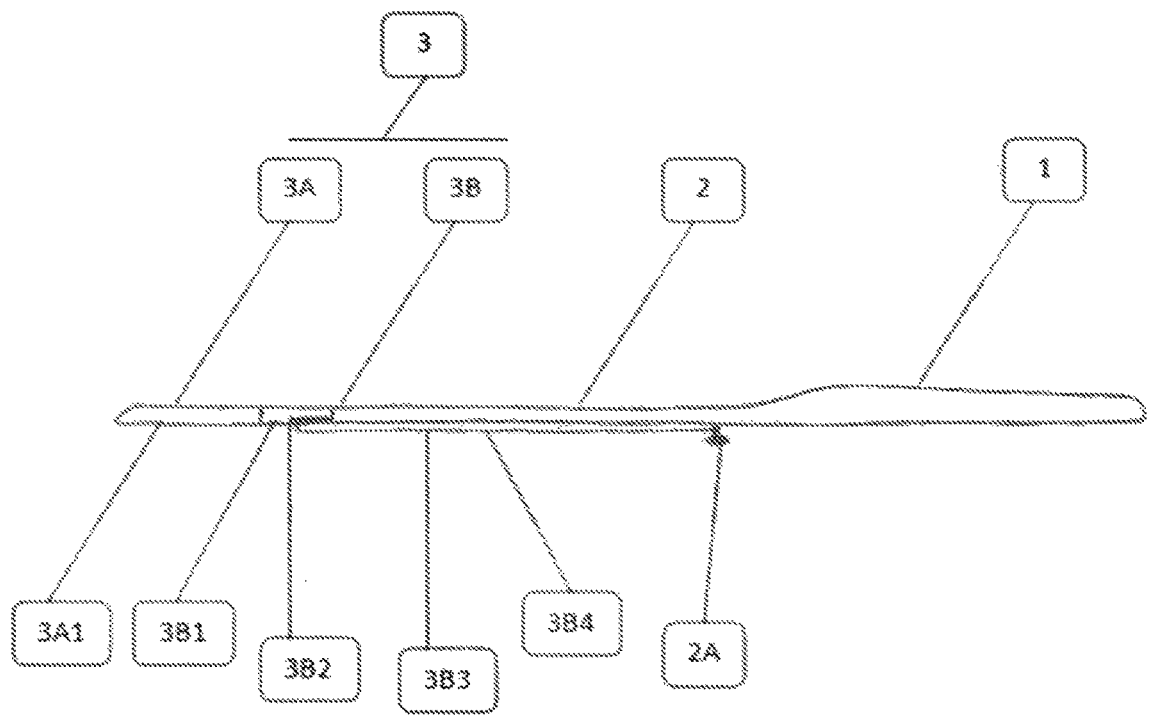
FIG. 2 shows the lateral longitudinal view showing Handle (1), Neck (2) and Working End (3). Neck has a Knob (2A) to control Metallic Lid (3B3). Working end has Wrasping Part (3A) and Cutting Part (3B). Forward directed Teeth (3A1) on the ventral surface of Wrasping Part (3A). Chamber (3B1) and Sharp Blade (3B2) are on ventral surface of Cutting Part (3B) which are covered by movable Metallic Lid (3B3) and is connected with the Knob (2A) through Extension (3B4).
Figure 3:
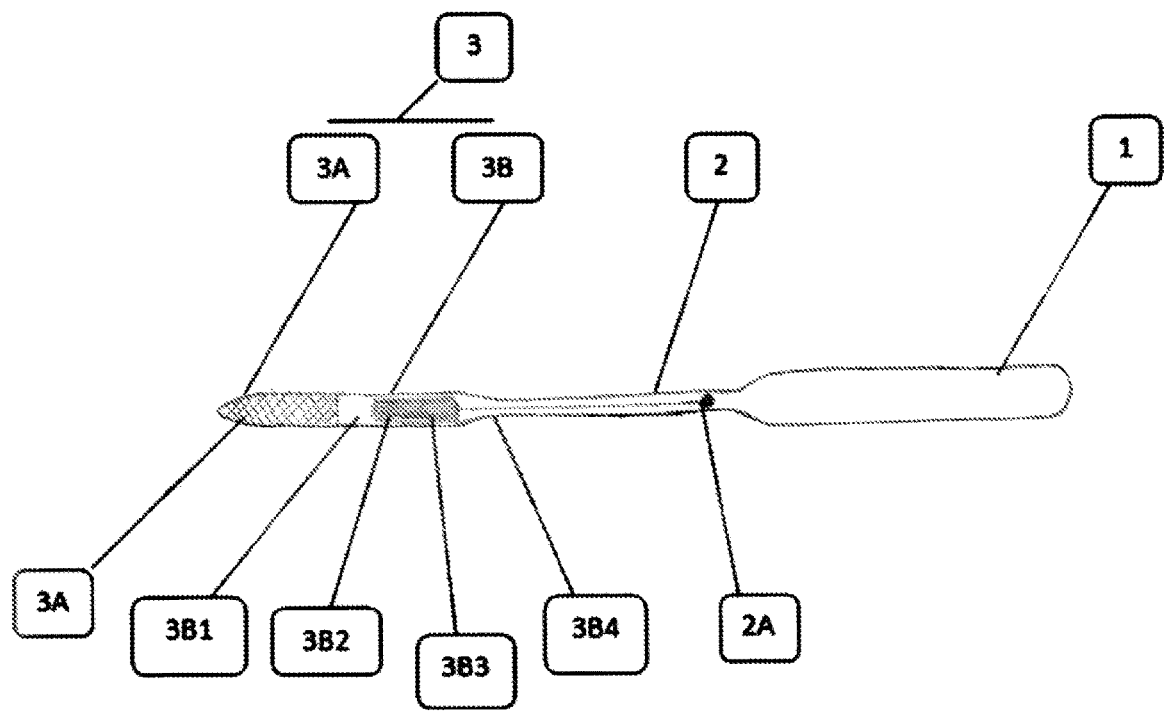
FIG. 3 shows the ventral view showing Handle (1), Neck (2) and Working End (3). Neck has a Knob (2A) to control Metallic Lid (3B3). Working end has Wrasping Part (3A) and Cutting Part (3B). Forward directed Teeth (3A1) on the ventral surface of Wrasping Part (3A). Chamber (3B1) and Sharp Blade (3B2) are on ventral surface of Cutting Part (3B) which are covered by movable Metallic Lid (3B3) and is connected with the Knob (2A) through Extension (3B4).

What is claimed:

1. A surgical device for removal of dorsal nasal hump, comprising:
   a handle (1) 30 mm broad, 100 mm long and 10 mm thick; connected to a rounded neck (2), 40 mm long and 5 mm thick wherein the rounded neck (2) is further connected to a working end (3), 8 mm broad; positioned at distal part of the handle (1) whereas the working end (3) has a semicircular tip and flat under surface (3A1); wherein the flat under surface consists of two parts including a wrasping part (3A) 30 mm thick with tapered and blunt tip; and a cutting part (3B), 30 mm thick wherein the cutting part is positioned between the rounded neck (2) and the wrasping part (3A); the cutting part (3B) further comprises a collecting chamber (3B1), 10 mm long, 6 mm wide and 3 mm deep; and a sharp blade (3B2), 6 mm wide, positioned at proximal edge of the collecting chamber; a metallic lid (3B3), 20 mm long and 7 mm wide disposed longitudinally, having a knob (2A) positioned on the metallic lid (3B3), used to slide the metallic lid back and forth to cover and uncover the flat under surface simultaneously.

2. The surgical device of claim 1 wherein total length of the device is 200 mm.

3. The surgical device of claim 1 wherein the device metal is autoclavable and steam sterilizable.

4. The surgical device of claim 1 wherein the device is made up of titanium or steel.

5. The surgical device of claim 1 wherein the wrasping Part (3A) contains criss-cross forwardly directed teeth (3A1) for wrasping a bone.

6. The surgical device of claim 1 wherein the device is used for removal of dorsal nasal hump and is observed through visual and tactile senses.

7. An application of surgical device of claim 1 for removal of dorsal nasal hump, consisting steps:
   holding the surgical device at the handle (1) and introduce into small cut made inside the nose;
   keeping the metallic lid (3B3) closed;
   pushing the working end (3) through its tapering and blunt tip for making a tunnel inside a nasal dorsum;
   uncovering the sharp blade (3B2) and the chamber (3B1) by moving the knob (2A) backward while the surgical device is inside a nasal dorsum;
   cutting the cartilaginous part of hump by to and fro movements of the working end;
   closing the metallic lid (3B3) by moving the knob (2A) forward, covering the sharp blade (3B2) and the chamber (3B1) both, and afterwards,
   wrasping the bony component of hump with the wrasping part (3A) by to and fro movements inside the tunnel.

* * * * *